US010285969B2

(12) United States Patent
Teng et al.

(10) Patent No.: US 10,285,969 B2
(45) Date of Patent: May 14, 2019

(54) MANGIFERIN-6-O-BERBERINE SALT AND PREPARATION METHOD AND USE THEREOF

(71) Applicants: CHANGZHOU DEZE MEDICAL SCIENCE CO., LTD, Jiangsu (CN); Houlei Teng, Jiangsu (CN); Wei Wu, Jiangsu (CN)

(72) Inventors: Houlei Teng, Jiangsu (CN); Wei Wu, Jiangsu (CN); Jingzhuo Zhang, Jilin (CN); Zhe Lin, Jilin (CN)

(73) Assignees: CHANGZHOU DEZE MEDICAL SCIENCE CO., LTD, Jiangsu (CN); Houlei Teng, Jiangsu (CN); Wei Wu, Jiangsu (CN)

( * ) Notice: Subject to any disclaimer, the term of this patent is extended or adjusted under 35 U.S.C. 154(b) by 36 days.

(21) Appl. No.: 15/619,936

(22) Filed: Jun. 12, 2017

(65) Prior Publication Data
US 2017/0273940 A1 Sep. 28, 2017

Related U.S. Application Data

(63) Continuation of application No. PCT/CN2016/070229, filed on Jan. 6, 2016.

(30) Foreign Application Priority Data

Jan. 7, 2015 (CN) .......................... 2015 1 0005381

(51) Int. Cl.
C07D 407/02 (2006.01)
C07D 407/04 (2006.01)
C07D 455/03 (2006.01)
A61K 31/352 (2006.01)
A61K 31/4375 (2006.01)
A61K 9/00 (2006.01)
A61K 9/20 (2006.01)
C07D 455/04 (2006.01)
A61K 9/06 (2006.01)
A61K 9/16 (2006.01)
A61K 9/19 (2006.01)
A61K 9/48 (2006.01)
A61P 3/00 (2006.01)

(52) U.S. Cl.
CPC .......... A61K 31/352 (2013.01); A61K 9/0095 (2013.01); A61K 9/06 (2013.01); A61K 9/1635 (2013.01); A61K 9/1652 (2013.01); A61K 9/19 (2013.01); A61K 9/20 (2013.01); A61K 9/2027 (2013.01); A61K 9/2054 (2013.01); A61K 9/2059 (2013.01); A61K 9/4866 (2013.01); A61K 31/4375 (2013.01); A61P 3/00 (2018.01); C07D 407/02 (2013.01); C07D 407/04 (2013.01); C07D 455/03 (2013.01); C07D 455/04 (2013.01)

(58) Field of Classification Search
CPC .. C07D 455/03; C07D 407/02; C07D 407/04; A61K 31/4375; A61K 31/352
See application file for complete search history.

(56) References Cited

U.S. PATENT DOCUMENTS 8,673,864 B2 * 3/2014 Teng ................... A61K 31/4375
514/23
2012/0094941 A1 4/2012 Teng et al.

FOREIGN PATENT DOCUMENTS

| CN | 101066275 A | 11/2007 |
| CN | 103816153 A | 5/2014 |
| EP | 2444094 A1 | 4/2012 |
| JP | 2012530078 | 11/2012 |
| WO | 2010145192 A1 | 12/2010 |

OTHER PUBLICATIONS

Andreu et al., "Mangiferin, a naturally occurring glucoxilxanthone improves long-term object recognition memory in rats" European Journal of Pharmacology vol. 635 pp. 124-128 (Year: 2010).*
Gomez-Zaleta et al., "UV/vis, 1H, and 13C NMR spectroscopic studies to determine mangiferin pKa values" Spectrochimica Acta Part A vol. 64 pp. 1002-1009 (Year: 2006).*
Li, Xuejian et al., Experimental Study on Hypoglycemic Effect of the Mixture of Mangiferin and Berberine, Modern Chinese Medicine, vol. 10, No. 12, pp. 26-28, 2008.
Li Ji, AMPK: New Treatment Target of Diabetes and Cardiovascular Diseases, China Medical Tribune, 2009, (1149).
Ren Junfang, AMPK and Cardiovascular Remodeling, Journal of International Pathology and Clinical Medicine, 2008, 28(1): 33-36.
Ricardo Lage, Carlos Dieguez, Antonio Vidal-Puig. et al., AMPK: Metabolic Gauge Regulating Whole-Body Energy Homeostasis, Trends Mol Med, 2008, 14(12): 539-49.
Fu Qingying, Gao Yuli, Advances in Studies of AMP-Activated Protein Kinase, Chinese Bulletin of Life Sciences, 17 (2): 147-152.
Chen Qi, Liang Houjie, Zou Lan, et al., Expression of Cyclooxygenase-2 by the Activation of Adenosine Monophosphate Protein Kinase and the Relationship Between the Expression and Chemosensitivity of 5-Fluorour-Acil in Colon Cancer. Practical Journal of Clinical Medicine, 2008, 5(3): 56-58.
State Intellectual Property Office of the P.R. China (ISR/CN), "International Search Report for PCT/CN2016/070229", China, dated Apr. 8, 2016.

(Continued)

Primary Examiner — Eric Olson
(74) Attorney, Agent, or Firm — Tim Tingkang Xia, Esq.; Locke Lord LLP

(57) ABSTRACT

The present invention provides a mangiferin-6-O-berberine salt and a preparation method thereof, and further provides a use of the mangiferin-6-O-berberine salt for the treatment of diabetics and other diseases as an AMPK activator.

13 Claims, No Drawings

(56) References Cited

OTHER PUBLICATIONS

Australian Government IP Australia, "1st Examination Report for Appln No. 2016206179", Australia, dated Feb. 15, 2018.
European Patent Office, "Extended European Search Report for 16734910.9", Munich, Germany, dated Jun. 14, 2018.
Japanese Patent Office, "1st Office Action for Appln No. 2017-536871", Japan, dated Apr. 27, 2018.
Russian Patent Office, "1st Office Action for Appin No. 2017123522/04", Australia, dated Jun. 21, 2018.
Khankari et al., "Pharmaceutical hydrates", Thermochimica Acta, 1995, pp. 61-79, vol. 248, Elsevier, USA.

\* cited by examiner

MANGIFERIN-6-O-BERBERINE SALT AND PREPARATION METHOD AND USE THEREOF

CROSS-REFERENCE TO RELATED APPLICATIONS

The present application is a continuation of international application No. PCT/CN2016/070229, filed on Jan. 6, 2016, which claims priority to Chinese Patent Application No. CN201510005381.7, filed on Jan. 7, 2015, both of which are hereby incorporated by reference in its entireties.

TECHNICAL FIELD

The present invention relates to a mangiferin-6-O-berberine salt, and a preparation method and use thereof as an AMPK activator.

BACKGROUND

Mangiferin is a natural polyphenol having a structural formula of $C_{19}H_{18}O_{11}$, a molecular weight of 422, and a chemical structure as follows:

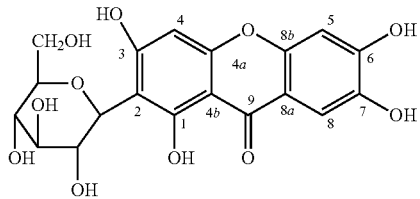

Berberine is isoquinoline alkaloid having a molecular formula: $[C_{20}H_{18}NO_4]^+$, a molecular weight of 336.37 and a chemical structure as follows:

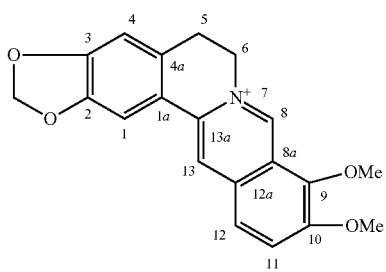

A mangiferin-berberine salt prepared by ionic bonding of mangiferin and berberine has been disclosed, International Publication Number: WO2010/145192A1, and entitled "MANGIFERIN-BERBERINE SALT, PREPARATION METHOD AND USE THEREOF".

At first, page 5 to the second paragraph on page 7 of the specification make a comparison between 13C-NMR spectrum, 1H-NMR spectrum of the mangiferin-berberine salt with a mangiferin and berberine prototype compound. It is thus concluded that the chemical environment of the atoms in the mangiferin and berberine groups has changed, which indicates that the mangiferin group and the berberine group are combined to form the mangiferin-berberine salt.

Analysis of the structure of the mangiferins shows that four phenolic hydroxy groups are present in the molecular structure of the mangiferin, the salt formation sites of the mangiferin have various possibilities, which increases the difficulty of yielding a mangiferin salt with a single salt formation site.

NMR data of the mangiferin-berberine salt disclosed in WO2010/145192A1 indicates that the mangiferin-berberine salt should be a composition of mangiferin3-O-berberine and mangiferin7-O-berberine. However, details about the mangiferin3-O-berberine and the mangiferin7-O-berberine, for example, the proportion of the mangiferin3-O-berberine and the mangiferin7-O-berberine, are not given in WO2010/145192A1.

Adenosine monophosphate (AMP)-activated protein kinase (AMPK) is a protein kinase which regulates energy metabolism in cells. A further development of the research on the AMPK finds that the AMPK plays a crucial role in the treatment of metabolic diseases, cardiovascular diseases, neurological diseases, inflammatory diseases, cancers and muscular system diseases. The AMPK is becoming a new target for the treatment of diseases. However, there is no AMPK activator in the market yet. The research and development of AMPK activators have important clinical significances (Li Ji, AMPK: New Treatment Target of Diabetes and Cardiovascular Diseases, *China Medical Tribune*, 2009, (1149); Ren Junfang, AMPK and Cardiovascular Remodeling, *Journal of International Pathology and Clinical Medicine*, 2008, 28(1): 33-36; Ricardo Lage, Carlos Dieguez, Antonio Vidal-Puig. et al., AMPK: Metabolic Gauge Regulating Whole-Body Energy Homeostasis, *Trends Mol Med*, 2008, 14(12): 539-49; Fu Qingying, Gao Yuli, Advances in Studies of AMP-Activated Protein Kinase, *Chinese Bulletin of Life Sciences*, 17(2): 147-152; Chen Qi, Liang Houjie, Zou Lan, et al., Expression of Cyclooxygenase-2 by the Activation of Adenosine Monophosphate Protein Kinase and the Relationship Between the Expression and Chemosensitivity of 5-Fluorour-Acil in Colon Cancer. *Practical Journal of Clinical Medicine*, 2008, 5(3): 56-58 and the like.

SUMMARY

According to the requirements of new drug application, the structure of new drug's active pharmaceutical ingredient must be clear and definite. If the active pharmaceutical ingredient is a composition, the proportion of the ingredients should be clearly defined to meet the requirement of quality control. Therefore, how to yield a mangiferin-berberine salt with a single salt formation site is a technical problem which is to be urgently solved for use of the mangiferin-berberine salt as a active pharmaceutical ingredient.

Secondly, a preparation method of the mangiferin-berberine salt is described in detail in the third paragraph to the third paragraph from the bottom on page 4 and Examples 1-6 as follows:

1. A solvent and mangiferin are added to a reactor to yield a suspension of mangiferin, and then an alkaline aqueous solution of sodium salt (potassium salt) is added to the suspension and reacted until the solution becomes clear. The resulted solution is filtrated to yield a solution A.

2. Berberine is added to water to dissolve, and then the solution is filtrated to yield a solution B.

3. The solution A is dropwise added slowly to the stirring solution B, and then the solution is continuously stirred for complete reaction. A precipitate is then produced. The resulted solution is filtrated to yield the precipitate. The precipitate is dried to yield the mangiferin-berberine salt.

The solvent described in the patent specification is any one or a mixture of water and one or at least two organic solvents which are miscible with water such as ethanol, methanol, acetone and the like. The volume proportion of water is 10-90% (v/v).

It is known from the preparation method disclosed in WO2010/145192A1 that a lot of organic solvents such as ethanol, methanol, acetone and the like are required, which are not only costly, but also pollute the environment in industrial production.

The present invention provides a mangiferin-6-O-berberine salt which has a structure as defined in the following formula (1):

carbonate, sodium bicarbonate, potassium carbonate and potassium bicarbonate; wherein the berberine hydrochloride is substitutable by a berberine sulfate or another medically acceptable salt of berberine.

The present invention further provides a drug, wherein the drug comprises the mangiferin-6-O-berberine as described above and pharmaceutically acceptable auxiliary material, The drug may be prepared to any acceptable formulations in clinically, oral preparations such as a tablet, a capsule, a granule, an oral solution, an oral suspension, a syrup, a pill and the like, external preparations such as gels, ointments, (I)

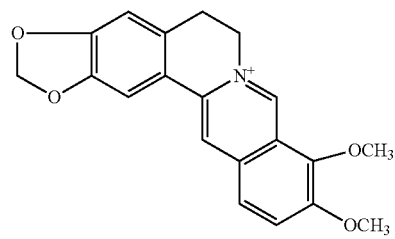 · 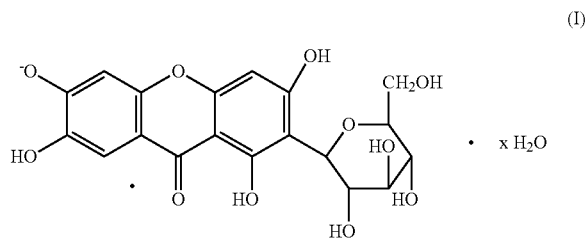 · x H$_2$O

In the formula (I), $0 \le x \le 4$.

In the mangiferin-6-O-berberine salt according to the present invention, x=2.

The present invention further provides a preparation method of the mangiferin-6-O-berberine salt. The method comprises the following steps:

(1) adding an alkaline sodium salt or a potassium salt into water to yield an alkaline aqueous solution on of sodium salt or an alkaline aqueous solution of potassium salt, the solution having a concentration of 0.1%-2% (w/v);

(2) dissolving mangiferin into dimethyl sulfoxide to yield a mangiferin solution;

(3) slowly adding the mangiferin solution into the alkaline aqueous solution of sodium salt or the alkaline aqueous solution of potassium salt, fully stirring the solutions until the solutions are fully reacted at the temperature of 50° C.-100° C. to yield a mangiferin-6-O-sodium salt solution or mangiferin-6-O-potassium salt solution;

(4) adding berberine hydrochloride into water at the temperature of 50° C.-100° C. to yield a solution of berberine hydrochloride;

(5) fully mixing the solution of berberine hydrochloride with the mangiferin-6-O-sodium salt solution or mangiferin-6-O-potassium salt solution for full reaction, yielding a precipitate, filtering the precipitate to yield a solid; and (6) drying the solid to yield the mangiferin-6-O-berberine salt In the preparation method of the mangiferin-6-O-berberine salt according to the present invention, a ratio of the mangiferin to the dimethyl sulfoxide is 1:0.2-5 (w/v).

In the preparation method of the mangiferin-6-O-berberine salt according to the present invention, a molar ratio of the mangiferin to the alkaline sodium salt or alkaline potassium salt is 1:0.5-1.

In the preparation method of the mangiferin-6-O-berberine salt according to the present invention, a molar ratio of the mangiferin-6-O-sodium salt or mangiferin-6-O-potassium salt to the berberine hydrochloride is 1:1.

In the preparation method of the mangiferin-6-O-berberine salt according to the present invention, the alkaline sodium salt or alkaline potassium salt is one or a mixture of more than two selected from the group consisting of sodium creams and the like, and injections such as freeze-dried powder injection and on the like.

The present invention further provides use of the mangiferin-6-O-berberine salt in the preparation of an AMPK activator.

The present invention further provides use of the drug prepared using the mangiferin-6-O-berberine salt as an activation ingredient in the preparation of the AMPK activator.

In view of the important role of the AMPK in the development of disease in modern medicine, the present invention provides use of the mangiferin-6-O-berberine in the preparation of an AMPK activator. The AMPK activator may be used for prevention or treatment of any one or more of the following diseases: diabetes, chronic diabetes complications (including coronary heart disease, atherosclerosis, cerebrovascular disease; diabetic nephropathy, diabetic retinopathy; neuropathy; diabetic foot; diabetic maculopathy, cataracts, glaucoma, refractive changes, iris and ciliary body disease and the like), obesity, hyperlipidemia, insulin resistance, hyperinsulinemia, metabolic syndrome, hypertension, atherosclerosis, ischemic heart disease, myocardial hypertrophy, arrhythmia, heart failure, upper respiratory tract infection, chronic bronchitis, chronic obstructive pulmonary disease, asthma, pulmonary fibrosis, hepatitis, simple fatty liver, non-alcoholic fatty liver disease, non-alcoholic steatohepatitis, alcoholic liver, alcoholic hepatitis, liver fibrosis, cirrhosis, prostatitis, pancreatitis, nephritis, nephrotic syndrome, hypertensive nephropathy, chronic renal insufficiency, rheumatic arthritis, rheumatoid arthritis, osteoarthritis, inflammatory bowel disease, cerebral infarction, memory impairment, Alzheimer's disease, infarct dementia, Parkinson's disease, tumors, muscle atrophy, and muscle weakness disease.

The present invention further provides use of the mangiferin-6-O-berberine salt in the preparation of drugs for the treatment of breast hyperplasia, uterine polyps, prostatic hyperplasia, sexual dysfunction, infertility, eczema, and fatigue.

An effective dose range of the mangiferin-6-O-berberine salt according to the present invention for the treatment of the above described diseases is 37.5-600 mg/day per person, preferably 75-300 mg/day per person; 1-3 times per day, preferably 2 times per day. Usage may be determined according to the specific disease, and oral administration is preferred.

Physical and Chemical Properties of the mangiferin-6-O-berberine salt:

Mangiferin-6-O-berberine salt: molecular formula: $C_{20}H_{18}NO_4 \cdot C_{19}H_{17}O_{11} \cdot xH_2O$; orange powder; melting point: 177-179° C.; almost insoluble in water, slightly soluble in methanol and dilute hydrochloric acid. The chemical structure of the mangiferin-6-O-berberine salt is as follows:

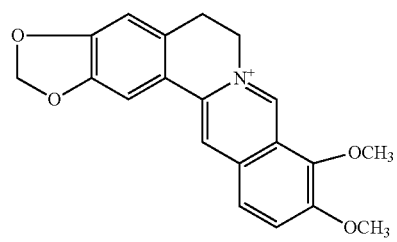 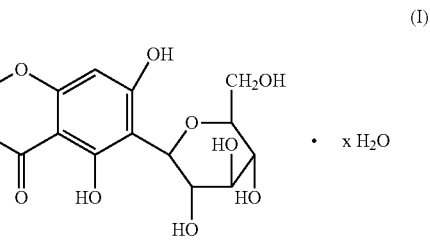

(I)

The spectrum data of the mangiferin-6-O-berberine salt is as follows: ESI-MS(−) m/z 756(M−), 421; ESI-MS(+) m/z 336, 423; the $^1$HNMR (400 MHz, DMSO-$d_6$) δ data of the mangiferin group is as follows: 4.56 (H-1'), 6.01 (H-5), 6.15 (H-4), 6.88 (H-8); the $^{13}$CNMR (400 MHz, DMSO-$d_6$) δ data of the mangiferin group is as follows: 161.51 (C-1), 106.58 (C-2), 163.06 (C-3), 92.77 (C-4), 155.55 (C-4a), 103.74 (C-4b), 98.64 (C-5), 166.93 (C-6), 147.03 (C-7), 100.47 (C-8), 100.53 (C-8a), 154.37 (C-8b), 176.73 (C-9), 73.51 (C-1'), 70.34 (C-2'), 79.14 (C-3'), 70.34 (C-4'), 81.37 (C-5'), 61.27 (C-6'); the $^1$HNMR (400 MHz, DMSO-$d_6$) δ data of berberine group is as follows: 3.2 (H-5), 4.03 (—OCH3), 4.07 (—OCH3), 4.89 (H-6), 6.13 (—O—CH2-O—), 7.01 (H-4), 7.69 (H-1), 7.86 (H-12), 8.07 (H-11), 8.78 (H-13), 9.78 (H-8); the $^{13}$CNMR (400 MHz, DMSO-$d_6$) δ data of the berberine group is as follows: 105.33 (C-1), 120.29 (C-1a), 147.56 (C-2), 149.71 (C-3), 108.22 (C-4), 130.45 (C-4a), 26.28 (C-5), 55.07 (C-6), 145.06 (C-8), 121.24 (C-8a), 143.51 (C-9), 150.15 (C-10), 126.55 (C-11), 123.33 (C-12), 132.87 (C-12a), 120.08 (C-13), 137.3 (C-13a), 56.93 (C10(—OCH$_3$)), 61.74 (C9(—OCH$_3$)), 101.96 (—O—CH$_2$—O—).

Addendum: The spectrum data of the mangiferin is as follows: ESI-MS m/z 421(M−); the $^1$HNMR (400 MHz, DMSO-$d_6$) δ data of the mangiferin is as follows: 4.60 (H-1'), 6.37 (H-5), 6.86 (H-4), 7.39 (H-8); the $^{13}$CNMR (400 MHz, DMSO-$d_6$) δ data of the mangiferin is as follows: 161.68 (C-1), 107.54 (C-2), 163.73 (C-3), 93.27 (C-4), 156.15 (C-4a), 101.25 (C-4b), 102.54 (C-5), 153.91 (C-6), 143.63 (C-7), 108.05 (C-8), 111.68 (C-8a), 150.7 (C-8b), 179.02 (C-9), 73.04 (C-1'), 70.24 (C-2'), 78.9 (C-3'), 70.56 (C-4'), 81.44 (C-5'), 61.41 (C-6').

The spectrum data of the berberine is as follows: ESI-MS m/z 336 (M); the $^1$HNMR (400 MHz, DMSO-$d_6$) δ data of the berberine is as follows: 3.26 (H-5), 4.11 (—OCH3), 4.21 (—OCH3), 4.92 (H-6), 6.11 (—O—CH2-O—), 6.96 (H-4), 7.66 (H-1), 8.0 (H-12), 8.11 (H-11), 8.7 (H-13), 9.76 (H-8); the $^{13}$CNMR (400 MHz, DMSO-$d_6$) δ data of the berberine is as follows: 106.54 (C-1), 121.49 (C-1a), 149.92 (C-2), 152.17 (C-3), 109.40 (C-4), 131.90 (C-4a), 28.24 (C-5), 57.20 (C-6), 145.73 (C-8), 123.33 (C-8a), 146.42 (C-9), 152.02 (C-10), 128.04 (C-11), 124.55 (C-12), 135.13 (C-12a), 121.86 (C-13), 139.65 (C-13a), 57.61 (C10(—OCH$_3$)), 62.56 (C9(—OCH$_3$)), 103.68 (—O—CH$_2$—O—).

Analysis of the above structure identification data is as follows:

Compared with a berberine prototype compound, the chemical shifts of carbon atom of the berberine group in mangiferin-6-O-berberine salt change remarkly due to shielding effect in the $^3$CNMR data.

Compared with a mangiferin prototype compound, the chemical shifts of $C_6$, $C_7$, $C_{8b}$ of the mangiferin group in mangiferin-6-O-berberine salt change remarkably due to the deshielding effect and the chemical shift of $C_6$ changes most remarkably among them; the chemical shifts of $C_5$, $C_8$, $C_{8a}$ also change to different degrees due to the shielding effect, and the chemical shifts of $C_8$ and $C_{8a}$ which lie in the meta position and para position of $C_6$ change more remarkably.

According to the above spectrum data analysis, it may be known that mangiferin-6-O$^−$ is combined with berberine-N$^+$, and the mangiferin-6-O-berberine salt is yielded.

The elemental analysis data of the mangiferin-6-O-berberine salt and the hydrates thereof is as follows:

| | Elemental analysis data of the mangiferin-6-O-berberine salt and hydrates thereof | | | | | |
|---|---|---|---|---|---|---|
| | Mass fraction, % | | | | | |
| | C | | H | | N | |
| Samples | Theoretical value | Measured value | Theoretical value | Measured value | Theoretical value | Measured value |
| Mangiferin-6-O-berberine salt | 61.82 | 61.57 | 4.62 | 4.70 | 1.85 | 1..84 |
| Mangiferin-6-O-berberine salt dihydrate | 59.02 | 58.73 | 4.92 | 4.93 | 1.77 | 1.72 |
| Mangiferin-6-O-berberine salt tetrahydrate | 56.45 | 56.24 | 5.19 | 5.20 | 1.69 | 1.67 |

After many years of researches, a new mangiferin-berberine salt with a single salt formation site has been successfully yielded, that is, a mangiferin-6-O-berberine salt.

The mangiferin-6-O-berberine salt not only solves the problem that the structure of new drug's active pharmaceutical ingredient should be clear, but also achieves the following unexpected technical effects compared with the mangiferin-berberine salt disclosed in WO2010/145192A1.

1. The solubility of the mangiferin-6-O-berberine salt according to the present invention is much higher than that of the mangiferin-berberine salt described in WO2010/145192A1 in a hydrochloric acid, such that the mangiferin-6-O-berberine salt is more simply dissolved in the stomach and is better absorbed. In a hydrochloric acid solution of pH 1, the solubility of the mangiferin-6-O-berberine salt is 12 mg/ml and the solubility of mangiferin-berberine salt disclosed in WO2010/145192A1 is 4 mg/ml, and the solubility of mangiferin-6-O-berberine salt is three times of the solubility of mangiferin-berberine salt disclosed in WO2010/145192A1. Furthermore, the stability of the mangiferin-6-O-berberine salt is better than that of the mangiferin-berberine salt disclosed in WO2010/145192A1.

2. The weight percentage of hygroscopicity of the mangiferin-6-O-berberine salt according to the present invention is much smaller than that of the mangiferin-berberine salt disclosed in WO2010/145192A1. The good stability under a high-humidity environment is beneficial for drug storage, thereby reducing the water absorption in the preparation of formulations and improving the quality of the drug.

3. It is accidentally found that the mangiferin-6-O-berberine salt according to the present invention exerts therapeutic effects on breast hyperplasia, uterine polyps, sexual dysfunction, prostatic hyperplasia, infertility, fatigue and eczema. These therapeutic effects cannot be predicted and acquainted according to the activity of the mangiferin-berberine salt disclosed in WO2010/145192A1.

Further a preparation method of the mangiferin-6-O-berberine salt is disclosed. Compared with the preparation method of the mangiferin-berberine salt disclosed in WO2010/145192A1, the preparation method according to the present invention solves the problem of the cost pressure and environmental issues which are brought due to use of a lot of organic solvents, and thus the preparation method according to the present invention is suitable for industrialized production. Furthermore, unexpected technical effects are achieved: a new mangiferin-berberine salt with a single salt formation site is yielded, that is, the mangiferin-6-O-berberine.

Comparison about the Solubility of Two Mangiferin-Berberine Salts in the Hydrochloric Acid Solution of pH 1

1. Test samples:
Sample A: Mangiferin-6-O-berberine salt dihydrate
Sample B: Mangiferin-berberine salt yielded using the method as disclosed in WO2010/145192A1.
2. Instrument: PHS-3C pH meter (Shanghai Kangyi)
3. Methods and Results:
Take pure water; add hydrochloric acid to adjust pH to 1 (25° C.±2° C.). Take the water 50 ml to different triangular flask; weigh up accurately 200 mg sample A and sample B which have been ground into powders and put them into the triangular flasks separately, shake and observe dissolved phenomena.

Sample A dissolve rapidly in the water of pH 1 and the solution is clear.

Sample B can dissolve in the water of pH 1 in 1 minute, but the solution becomes turbid soon, which indicates that some precipitate has been formed.

Take the water 50 ml to different triangular flasks; weigh up accurately sample A 400 mg and 600 mg which have been ground into powders and put the powders into the triangular flasks separately, shake and observe dissolving phenomena.

400 mg sample A dissolves rapidly in 50 ml water of pH 1 and the solution is clear. No precipitate is formed after standing 24 hours.

600 mg sample A dissolves rapidly in 50 ml water of pH 1 and the solution is clear. A little precipitate is formed about 30 minutes later and the solution is slightly turbid.

The above results indicate that the solubility of sample A in the hydrochloric acid solution of pH 1 is about 12 mg/ml; the solubility of sample B in the hydrochloric acid solution of pH 1 is about 4 mg/ml; and the stability of the solution of the mangiferin-6-O-berberine salt is much better than the mangiferin-berberine salt disclosed in in WO2010/145192A1.

4. Conclusion:
The solubility of mangiferin-6-O-berberine salt in the hydrochloric acid solution of pH 1 is three times over the mangiferin-berberine salt disclosed in WO2010/145192A1.

Comparison about the Stability of Two maniferin-berberine salts under a High-Humidity Environment 1. Test Samples
Sample A: Mangiferin-6-O-berberine salt dihydrate
Sample B: Mangiferin-berberine salt yielded using the method as disclosed in WO2010/145192A1.
2. Instrument: One ten-thousandth electronic balance (Sartorius, Germany)
3. Investigation Method:
Weigh up accurately appropriate amount sample A in 3 glass gardens and sample B in 3 glass gardens separately; put the samples in a drug stability chamber with the condition being set to: 25° C./90% RH±5% RH and storage for 10 days. Weigh the samples accurately on the fifth day and tenth day; record the results of weighing and calculate weight percentage of moisture absorption.
4. the Results are as Follows:

|  | Compound | The percentage of 5-day weight gain (%) | The percentage of 10-day weight gain (%) |
| --- | --- | --- | --- |
| Sample A | mangiferin-6-O-berberine salt dihydrate | 3.2 | 4.8 |
| Sample B | mangiferin-berberine salt | 5.3 | 8.7 |

5. Discussion:
The weight percentage of moisture absorption of the mangiferin-6-O-berberine salt dihydrate is much smaller than that of the mangiferin-berberine salt as disclosed in WO2010/145192A1 under a high humidity environment.

Activation of Mangiferin-6-O-Berberine Salt on AMPK

1. Materials
The mangiferin-6-O-berberine salt dihydrate yielded using the method as disclosed in the above examples dissolves in DMSO. Before use, the mangiferin-6-O-berberine salt dihydrate is diluted by a culture medium or HBS. The ultimate concentration of DMSO is no more than 0.2%.

The rat L6 cell line is purchased from the ATCC. HG-DMEM is purchased GIBCO™. Fetal bovine serum (FBS) is purchased from Hyclone. Anti-AMPK, anti-ACC, antiphospho-AMPK (Thr172), antiphospho-ACC (ser79) polyclonal antibodies are purchased from Cell Signal Technology.

2. Methods
2.1 Cell Culture
L6 cells were grown in HG-DMEM containing 10% (v/v) FBS, 100 U/ml penicillin and 100 U/ml streptomycin in a humidified atmosphere of 5% CO2 at 37° C. When the cells covered 60%, the medium was switched to HG-DMEM with 2% FBS and the culture medium was replaced every two days until the cells differentiation reached 90%.

2.2 the Treatment and Collection of Samples

Cells in 6-well plates were starved in serum-free HG-DMEM, and then different concentration gradient samples were added into serum-free HG-DMEM; the concentration of DMSO is 0.2%. The samples incubated for 3 hours in the cells. Cells were rinsed twice with ice-cold 1×PBS and lysed with 200 μl 1×SDS loading buffer (50 mM Tris·HCL, 100 mM DTT, 2% SDS, 0.1% bromophenol blue, 10% glycerol) for 10 minutes. Collected lysis buffer, ultrasound for 15 seconds, boiled at 100° C. for 10 minutes.

2.3 Western Blot

Samples were electrophoresed on 10% SDS-polyacrylamide gels, and transferred to PVDF membranes under 100V and 1-2 hours in the transmembrane instrument. Protein in the gel was transferred to nitrocellulose membrane under the state of half dry, and the band was determined by Ponceau S (Ponceau S). The membrane was closed in a blocking solution (3% nonfat dry milk, 0.1% Tween, TBS solution) for 1 hour; primary antibodies were added at 1:1000 at 4° C. overnight, washed by TBS for 3×15 min; the secondary antibodies were added at 1:1000, incubated for 1 hour at the room temperature, washed by TBS for 3×15 min, placed on the ECL and washed for 5-10 min, and imaged by X-ray.

3. Results

The mangiferin-6-O-berberine salt (1.25-5 μmol/L) enhances significantly the phosphorylation of both AMPK and ACC in a dose-dependent manner.

Effects of Mangiferin-6-O-Berberine Salt on the Improvement of Metabolic Disorder Indices The patients according to the criteria of diagnosing non-alcoholic fatty liver combined with type 2 diabetes mellitus oral administrated mangiferin-6-O-berberine salt tablets 75 mg (for the preparation method, reference may be made to Example 6) two times per day. Six months later, the liver enzymes (ALT, AST), hepatic steatosis (by Color Doppler ultrasound), the index of APRI (indicating hepatic fibrosis), glycosylated hemoglobin (HbA1C), serum insulin (INS), insulin sensitivity index (ISI), blood lipid (TG), blood pressure (systolic and diastolic blood pressure), urine microalbumin and weight of patients was bettered significantly.

The results indicate that mangiferin-6-O-berberine salt exerts the effects as follows: decreasing liver enzymes, improving hepatic steatosis, improving hepatic fibrosis and hypoglycemic action, decreasing insulin, increasing insulin sensitivity and hypolipidemic action, reducing blood press, decreasing urine microalbumin and decreasing weight.

Details are as follows:

| Indices of before and after administration of mangiferin-6-O-berberine salt (n = 8, mean ± SD) | | |
|---|---|---|
| | Base line (before administration) | Mangiferin-6-O-berberine salt |
| ALT (U/L) | 136.50 ± 18.25 | 51.85 ± 7.22* |
| AST (U/L) | 83.32 ± 10.21 | 39.20 ± 4.22* |
| Liver color Doppler ultrasound | fatty liver | normal |
| APRI index | 0.447 ± 0.05 | 0.203 ± 0.03* |
| $HbA_1C$ (%) | 7.18 ± 0.36 | 5.80 ± 0.11* |
| INS (pmol/L) | 197.99 ± 19.26 | 56.08 ± 18.05* |
| ISI | −7.12 ± 0.12 | −5.80 ± 0.30* |
| TG (mmol/L) | 3.56 ± 0.89 | 1.41 ± 0.44* |
| Atherogenic index (AI) | 4.12 ± 0.79 | 3.10 ± 0.84* |
| Systolic pressure (mmHg) | 153.77 ± 9.03 | 125.86 ± 0.01* |
| Diastolic pressure (mmHg) | 94.79 ± 3.70 | 76.39 ± 0.51* |
| Weight (kg) | 73.35 ± 3.02 | 62.34 ± 2.11* |
| Urine microalbumin ($1^+$ is seen as 1) | 0.60 ± 0.02 | 0 ± 0* | p.s.: *$p < 0.05$

Effects of Mangiferin-6-O-Berberine Salt Tablets on the Treatment of Bodies

The mangiferin-6-O-berberine salt tablets were orally administrated (A for short, for the preparation method, reference may be made to Example 6). It is found that the mangiferin-6-O-berberine salt exerts the therapeutic effects on: rheumatoid arthritis, hyperplasia of mammary glands, uterine polyp, prostatic hyperplasia, dementia, sexual dysfunction, infertility, arrhythmia, heart failure and fatigue. The mangiferin-6-O-berberine salt gels (B for short, for the preparation method, reference may be made to Example 10) were applied on the affected area. It is discovered that the mangiferin-6-O-berberine salt exerts the therapeutic effects on eczema. Details are as follows:

| The treatment of mangiferin-6-O-berberine salt on diseases (mean ± SD) | | | | | | |
|---|---|---|---|---|---|---|
| | | | Course | | Improvement of index | |
| Disease name | n | Usage and dose | of treatment | Index | before administration | after administration |
| Rheumatoid arthritis | 8 | A, 75 mg, 2 times per day | 6 months | DAS28 score | 3.18 ± 0.29 | 1.80 ± 0.42* |
| Breast hyperplasia | 8 | A, 37.5 mg, 3 times per day | 3 months | Lump ($mm^2$, color Doppler ultrasound) | 63.00 ± 12.55 | 23.18 ± 2.89* |
| Uterine polyps | 8 | A, 37.5 mg, 2 times per day | 3 months | Polyps ($mm^2$, color Doppler ultrasound) | 56.77 ± 7.81 | 0 ± 0* |
| Prostatic hyperplasia | 8 | A, 300 mg, 2 times per day | 6 months | Prostate ($mm^2$, color Doppler ultrasound) | 14.19 ± 2.69 | 10.66 ± 2.12* |
| | | | | IPSS integral | 9.21 ± 0.88 | 7.38 ± 0.61* |
| Dementia | 8 | A, 150 mg, 2 times per day | 12 months | MMSE integral | 18.11 ± 3.24 | 23.59 ± 4.74* |

The treatment of mangiferin-6-O-berberine salt on diseases (mean ± SD)

| Disease name | n | Usage and dose | Course of treatment | Index | Improvement of index before administration | Improvement of index after administration |
|---|---|---|---|---|---|---|
| Sexual dysfunction | 8 | A, 150 mg, 2 times per day | 6 months | HEF-5 integral | 10.47 ± 2.13 | 18.97 ± 3.68* |
| Infertility | 10[8] | A, 75 mg, 2 times per day | 6 months | Pregnancy rate (%) | 0 | 30 |
| Arrhythmia | 8 | A, 75 mg, 2 times per day | 3 months | electrocardiogram PR interval (ms) | 248.33 ± 25.81 | 204.50 ± 14.99* |
| Chronic heart failure | 8 | A, 75 mg, 2 times per day | 3 months | Left ventricular ejective fraction(%) | 50.12 ± 6.99 | 59.32 ± 7.16* |
| Fatigue | 10 | A, 37.5 mg, 1 time per day | 3 months | FAI score | 120.33 ± 25.19 | 100.92 ± 19.15* |
| Eczema | 8 | B, appropriate amount, 1 time per day | 7 days | SCORAD score | 19.11 ± 3.76 | 10.63 ± 2.08* | p.s.: *$p < 0.05$, #10 couples

Pharmacokinetic Comparison Between the Mangiferin-6-O-Berberine Salt and the Mangiferin-Berberine Salt 1. Test schemes:

Sample A: Mangiferin-6-O-berberine salt dihydrate

Sample B: Mangiferin-berberine salt yielded using the method disclosed in WO2010/145192A1.

A single intragastric administration of sample of A or B was given to SD rats at the dosage of 100 mg/kg and blood was sampled from jugular vein at 0, 0.083, 0.25, 0.5, 1, 1.5, 2, 3, 4, 5, 6, 7, 8, 12 and 24 h.

Preparation of the mangiferin reference solution: Mangiferin reference was weighed accurately and put into a 25 ml volumetric flask; methanol was added to make mangiferin dissolve, diluted to graduation. The mangiferin reference mother liquor is yielded for reserve. An appropriate amount of mangiferin reference mother liquor was taken out accurately and diluted to prepare the mangiferin reference solutions having a concentration of 2, 5, 10, 50, 100, 200 ng/ml.

Preparation of the berberine hydrochloride reference solution: The berberine hydrochloride reference was weighed accurately and put into a 25 ml volumetric flask; methanol was added to make the berberine hydrochloride dissolve, and dilute to graduation. The berberine hydrochloride reference mother liquor was yielded for reserve. An appropriate amount of berberine hydrochloride reference mother liquor was taken out accurately and diluted to prepare reference solution whose berberine concentration is 0.2, 0.5, 2, 10, 20, 50 ng/ml.

Preparation of the internal standard solution: Glibenclamide was weighed accurately and put into a 25 ml volumetric flask; acetonitrile was added to make glibenclamide dissolve, and dilute to graduation. The internal standard solution of glibenclamide was yielded, having a concentration of 50 ng/ml.

Blood sample processing method: Rat blood was put in a heparin anticoagulant centrifuge tube and centrifuged for 10 minutes at 6000 rpm, and the plasma was taken for reserve at −20° C.

The treatment of the blank plasma: take 100 ul plasma, add the solution of acetonitrile-acetic acid (9:1) 500 ul, vortex for 5 minutes, centrifugation for 10 min at 6000 rpm, take the supernatant, vacuum dry at 50° C., add 100 ul added mobile phase into the residue, vortex for 3 minutes, centrifugation for 10 minutes at 6000 rpm. Blank plasma sample is obtained and 10 ul supernatant is injected.

The treatment of the administration plasma sample: take 100 ul administration plasma at every blood sampling time point separately, add the solution of acetonitrile-acetic acid (9:1) 500 ul, vortex for 5 minutes, centrifugation for 10 min at 6000 rpm, take the supernatant, vacuum dry at 50° C., add 100 ul added mobile phase into the residue, vortex for 3 minutes, centrifugation for 10 minutes at 6000 rpm. Administration plasma sample is obtained and 10 ul supernatant is injected.

Chromatographic conditions: mobile phase A: 0.1% formic acid, mobile phase B: methanol; chromatographic column: Waters Xbridge C18 (50*2.1 mm, 5 um); flow rate: 0.40 mL/min.

Gradient Elution Method:

| Time (min) | Mobile phase B (%) |
|---|---|
| 0.50 | 18 |
| 1.20 | 98 |
| 2.50 | 98 |
| 2.51 | 18 |
| 4.00 | Stop |

Mass spectrometry conditions: ion detection mode: multi ion detection (MRM); ion polarity: positive ion; mangiferin: m/z 422.9/327.1, berberine: m/z 337.3/321.3, internal standard: m/z 494.2/369.1.

2. Results

The pharmacokinetic parameters are calculated with a non compartmental model in Pharsight Phoenix 6.3.

| The AUC of mangiferin-6-O-berberine salt and mangiferin-berberine salt (mean ± SD) | | | | |
|---|---|---|---|---|
| | Mangiferin-6-O-berberine salt (n = 3) | | Mangiferin-berberine salt (n = 3) | |
| Parameter | Mangiferin | Berberine | Mangiferin | Berberine |
| $AUC_{0-t}$(ng*h/ml) | 1831.11 ± 510.25 | 669.72 ± 312.83 | 834.21 ± 305.34 | 275.04 ± 114.22 |

The results show that the AUC of mangiferin-6-O-berberine salt is 2 times over that of the mangiferin-berberine salt by oral administration, which shows that the absorption of mangiferin-6-O-berberine salt is higher than that of the mangiferin-berberine salt.

Preparation of Mangiferin-6-O-Berberine Salt Dihydrate 670 ml water was added into a reactor and 0.1 mol potassium bicarbonate was dissolved in water to yield a solution of potassium bicarbonate having a concentration of 1.5% (w/v). 0.1 mol mangiferin (42.2 g) was dissolved in 21 ml DMSO (the ratio of mangiferin to DMSO was 1:0.5 (w/v)) and then heated to yield a mangiferin solution. The mangiferin solution was added slowly into the solution of potassium bicarbonate, and then stirred sufficiently at 70° C. for complete reaction. Then the resulted solution was filtrated and the solution of mangiferin-6-O-potassium salt was yielded. The temperature was kept at 60° C. for reserve. 0.1 mol berberine hydrochloride was dissolved in 3700 ml water at 70° C. to yield the solution of berberine hydrochloride. The temperature was kept at 80° C. for reserve. Then the solution of mangiferin-6-O-potassium salt was added slowly into the solution of berberine hydrochloride, and then stirred sufficiently for complete reaction. Subsequently, a lot of precipitate was produced after standing. The resulted solution was filtrated to yield the precipitate, and the precipitate was then vacuum dried at 45° C. and 65.7 g orange mangiferin-6-O-berberine salt dihydrate solid was yielded. The productivity was 82.8%, and the purity of the product was 97.6% as detected by HPLC.

DETAILED DESCRIPTION

The mangiferin according to the present invention can be purchased from market (Xi'an Yanglingdongke Pharmaceutical Co., Ltd., and the mangiferin can be produced by any factory which has the corresponding equipment, wherein the content is 98%). The berberine hydrochloride and the berberine sulfate and on the like according to the present invention can be purchased from market (Xi'an Xiaocao Plant Technology Co., Ltd.). The reagent according to the present invention such as sodium carbonate, sodium bicarbonate, potassium carbonate, potassium bicarbonate, dimethyl sulfoxide and the like can be purchased from market.

Preparation Example 1: Preparation of Mangiferin-6-O-Sodium Salt 1700 ml water was added in a reactor and 0.1 mol sodium bicarbonate was dissolved in water to yield a solution of sodium bicarbonate having a concentration of 0.5% (w/v). 0.1 mol mangiferin (42.2 g) was dissolved in 85 ml DMSO (the ratio of mangiferin to DMSO is 1:2 (w/v)), heated and dissolved to yield a mangiferin solution. The mangiferin solution was added slowly to the solution of sodium bicarbonate, and stirred sufficiently at 85° C. for complete reaction. Then, the resulted solution was filtrated. When the temperature of resulted solution fell to the room temperature, 2 times volume acetone was added to the solution and stirred sufficiently. Subsequently, a lot of precipitation was produced. The resulted solution was filtrated to yield the precipitate and the precipitate was washed adequately by ethanol. Then, the precipitate was vacuum dried at 40° C. and crushed to yield 21.3 g faint-yellow mangiferin-6-O-sodium salt powder. The productivity was 50.5%, and the purity of the product was 98.6% as detected by HPLC.

The data of the mangiferin-6-O-sodium salt is as follows: $^1$HNMR (400 MHz, DMSO-$d_6$) δ: 4.60 (H-1'), 6.01 (H-5), 6.10 (H-4), 6.96 (H-8); $^{13}$CNMR (400 MHz, DMSO-$d_6$) (δ ppm): 162.43 (C-1), 106.82 (C-2), 161.56 (C-3), 93.50 (C-4), 157.12 (C-4a), 101.06 (C-4b), 99.53 C-5), 161.56 (C-6), 147.08 (C-7), 103.75 (C-8), 106.83 (C-8a), 154.28 (C-8b), 176.63 (C-9), 73.67 (C-1'), 70.24 (C-2'), 79.19 (C-3'), 70.24 (C-4'), 81.05 (C-5'), 60.97 (C-6').

Preparation Example 2: Preparation of Mangiferin-6-O-Potassium Salt 1700 ml water was added into a reactor and 0.05 mol potassium carbonate was dissolved in water to yield a solution of potassium carbonate having a concentration of 0.8% (w/v). 0.1 mol mangiferin (42.2 g) was dissolved in 42 ml DMSO (the ratio of mangiferin to DMSO was 1:1 (w/v)) then heated to yield potassium carbonate, and stirred sufficiently at 60° C. to for complete reaction. The resulted solution was filtrated. When the temperature of resulted solution fell to 40° C., 2 times volume acetone was added and the solution was stirred sufficiently. Subsequently, a lot of precipitate was produced. The resulted solution was filtrated to yield the precipitate and the precipitate was washed adequately by ethanol. Then the precipitate was vacuum dried at 50° C. and crushed to yield 25.3 g faint-yellow mangiferin-6-O-sodium salt powder. The productivity was 60.2%, and the purity of the product was 98.3% as detected by HPLC.

Example 1: Preparation of Mangiferin-6-O-Berberine Salt 2000 ml water was added into a reactor and 0.1 mol sodium bicarbonate was dissolved in water to yield a solution of sodium bicarbonate having a concentration of 0.4% (w/v). 0.1 mol mangiferin (42.2 g) was dissolved in 127 ml DMSO (the ratio of mangiferin to DMSO was 1:3 (w/v)), and then heated to yield a mangiferin solution. The mangiferin solution was added slowly into the solution of sodium bicarbonate, and stirred sufficiently at 80° C. for complete reaction. Then the resulted solution was filtrated to yield a solution of mangiferin-6-O-sodium salt. The temperature was kept at 60° C. for reserve. 0.1 mol berberine hydrochloride was dissolved in 2000 ml water at 60° C. to yield a solution of berberine hydrochloride. The temperature was kept at 60° C. for reserve. The solution of mangiferin-6-O-sodium salt was added slowly to the solution of berberine hydrochloride, stirred sufficiently for complete reaction. Subsequently, a lot of precipitate was produced after standing. The resulted solution was filtrated to yield the precipitate and then the precipitate is vacuum dried at 60° C. The dried product was added into proper DMSO to dissolve, and then the solution of DMSO was added into proper acetone, and then stirred sufficiently. Subsequently, a lot of precipitate was produced after standing. The resulted solution was filtrated to yield the precipitate and the precipitate was then was washed adequately by ethanol. Then, the deposition was vacuum dried at 55° C. and 52.0 g orange mangiferin-6-O-berberine salt solid was yielded. The productivity was 65.6%, and the purity of the product was 95.6% as detected by HPLC.

Example 2: Preparation of the Mangiferin-6-O-Berberine Salt Dihydrate 3500 ml water was added into a reactor and 0.05 mol sodium carbonate was dissolved in water to yield a solution of sodium carbonate having a concentration of 0.3% (w/v). 0.1 mol mangiferin (42.2 g) was dissolved in 169 ml DMSO (the ratio of mangiferin to DMSO was 1:4 (w/v)) to yield a mangiferin solution. The mangiferin solution was added slowly into a solution of sodium carbonate, and stirred sufficiently at 100° C. to react completely. Then a solution of mangiferin-6-O-sodium salt is yielded. The temperature was kept at 80° C. for reserve. 0.1 mol berberine hydrochloride was dissolved in 3700 ml water at 90° C. to yield a solution of berberine hydrochloride. The temperature was kept at 80° C. for reserve. Then the solution of berberine hydrochloride was added slowly into the solution of mangiferin-6-O-sodium salt, and then stirred sufficiently for complete reaction. Subsequently, a lot of precipitate was produced after standing. The resulted solution was filtrated to yield the precipitate, and the precipitate was then vacuum dried, and 57.0 g orange mangiferin-6-O-berberine salt dihydrate solid was yield. The productivity was 71.8%, and the purity of the product was 94.5% as detected by HPLC.

Example 3: Preparation of Mangiferin-6-O-Berberine Salt Dihydrate 13800 ml water was added into a reactor and 0.06 mol potassium carbonate was dissolved in water to yield a solution of potassium carbonate having a concentration of 0.1% (w/v). 0.1 mol mangiferin (42.2 g) was dissolved in 210 ml DMSO (the ratio of mangiferin to DMSO was 1:5 (w/v)) to yield a mangiferin solution. The mangiferin solution was added slowly into the solution of potassium carbonate, and the stirred sufficiently at 50° C. to for complete reaction. Then, a solution of mangiferin-6-O-potassium salt was yielded. The temperature was kept at 40° C. for reserve. 0.1 mol berberine sulfate was dissolved in 870 ml water at 50° C. and then the resulted solution was filtrated to yield a solution of berberine sulfate. The temperature was kept at 40° C. for reserve. Then the solution of berberine sulfate was added slowly into the solution of mangiferin-6-O-potassium salt, and stirred sufficiently for complete reaction. Subsequently, a lot of precipitate was produced after standing. The resulted solution was filtrated to yield the precipitate, the precipitate was then vacuum dried at 50° C., and 48.2 g orange mangiferin-6-O-berberine salt dihydrate solid was yielded. The productivity was 57.6%, and the purity of the product was 95.5% as detected by HPLC.

Example 4: Preparation of Mangiferin-6-O-Berberine Salt Tetrahydrate 800 ml water was added into reactor and 0.1 mol sodium bicarbonate was dissolved in water to yield a solution of sodium bicarbonate having a concentration of 1% (w/v). 0.1 mol mangiferin (42.2 g) was dissolved in 8.5 ml DMSO (the ratio of mangiferin to DMSO was 1:0.2 (w/v)), and heated to yield a mangiferin solution. The mangiferin solution was added slowly into the solution of sodium bicarbonate, and the stirred sufficiently at 90° C. to for complete reaction. Then the resulted solution was filtrated and the solution of mangiferin-6-O-sodium salt was yielded. The temperature was kept at 80° C. for reserve. 0.1 mol berberine hydrochloride was dissolved in 37000 ml water at 80° C. to yield a solution of berberine hydrochloride. The temperature was kept at 70° C. for reserve. Then the solution of mangiferin-6-O-sodium salt was added slowly into the solution of berberine hydrochloride, and then stirred sufficiently for complete reaction. Subsequently, a lot of precipitate was produced. The resulted solution was filtrated to yield the precipitate, and the precipitate was washed adequately by water. Then the precipitate was dried, and 56.2 g dried product was yielded. The productivity was 70.8%. The dried product was recrystallized in methanol and 35.9 g orange mangiferin-6-O-berberine salt tetrahydrate was yielded. The productivity was 44.3%, and the purity of the product was 97.5% as detected by HPLC.

Example 5: Preparation of the Mangiferin-6-O-Berberine Salt Dihydrate 380 ml water was added into a reactor and 0.04 mol sodium carbonate and 0.04 mol sodium bicarbonate were dissolved in water to yield a alkaline aqueous solution of sodium salt having a concentration of 2% (w/v). 0.1 mol mangiferin (42.2 g) was dissolved in 50 ml DMSO (the ratio of mangiferin to DMSO is 1:1.2 (w/v)) and heated to yield a mangiferin solution. Then the mangiferin solution was added slowly into the alkaline aqueous solution of sodium salt, and the stirred sufficiently at 95° C. for complete reaction. Then the resulted solution was filtrated and the solution of mangiferin-6-O sodium salt was yielded. The temperature was kept at 90° C. for reserve. 0.1 mol berberine hydrochloride was dissolved in 3700 ml water at 100° C. to yield a solution of berberine hydrochloride. The temperature was kept at 90° C. for reserve. Then the solution of berberine hydrochloride was added slowly into the solution of mangiferin-6-O sodium salt, and then stirred sufficiently for complete reaction, cooling and standing. Subsequently, a lot of precipitate was produced. The resulted solution was filtrated to yield the precipitate, the precipitate was then vacuum dried at 55°, and finally 64.9 g orange mangiferin-6-O-berberine salt dihydrate was yielded. The productivity was 81.8%, and the purity of the product was 96.5% as detected by HPLC.

Example 6: Preparation of Mangiferin-6-O-Berberine Salt Tablets

The Mangiferin-6-O-berberine salt dihydrate yielded using the method disclosed in the above examples was smashed and subjected to a 160-mesh sieve. 37.5 g mangiferin-6-O-berberine salt was weighed, and then 50 g microcrystalline cellulose and 45 g pregelatinized starch were added as diluting agents, and the mixture was then mixed uniformly. An ethanol solution of 10% polyvinyl pyrrolidone K30 was used as a bonding material to prepare a soft material; and the mixture was granulated using a 24-mesh sieve, and then subjected to breaking and drying. 0.5% octadecanoic acid and 2% micro powder silica gel were added as lubricants; and the mixed uniformly and tableted. Finally the tablets were film coated, 1000 film-coated tablets were prepared. Each tablet contained 37.5 mg mangiferin-6-O-berberine salt.

Example 7: Preparation of Mangiferin-6-O-Berberine Salt Granule

The mangiferin-6-O-berberine salt yielded using method disclosed in the above examples was mashed and the subjected to a 160-mesh sieve. 103 g mangiferin-6-O-berberine salt was weighed, 150 g pregelatinized starch was added as diluting agents, and 100 g xylose was added as a flavoring agent. The mixture was then mixed uniformly. A solution of 1% carboxymethylcellulose sodium was used as a bonding material to prepare a soft material. The mixture was granulated using a 24-mesh sieve, and then subjected to breaking and drying. Granules were yielded after packaging. The content of mangiferin-6-O-berberine salt was 42 mg/g.

Example 8: Preparation of Mangiferin-6-O-Berberine Salt Capsules

The mangiferin-6-O-berberine salt dihydrate yield using the method disclosed in the above examples was smashed and then subjected to a 160-mesh sieve. 75 g powder was weighed. 20 g microcrystalline cellulose and 25 g starch were added as diluting agents, and the mixture was then mixed uniformly. An ethanol solution of 10% polyvinyl pyrrolidone K30 was used as a bonding material to prepare a soft material, The mixture was granulated using a 24-mesh sieve, and the subjected to breaking and drying. Finally, 1000 capsules were yielded after packaging. Each capsule contained 75 mg mangiferin-6-O-berberine salt.

Example 9: Preparation of Mangiferin-6-O-Berberine Salt Gels 15 g hydroxypropyl methyl cellulose and 10 g sodium alginate were weighed, and then an appropriate amount of water was added. The resulted solution was then stirred sufficiently to dissolve and a substrate was yielded. 5 g mangiferin-6-O-berberine salt tetrahydrate was added into 100 ml dimethyl sulfoxide to dissolve, and then mixed with the substrate. 1000 ml well-distributed liquid was yielded, namely, mangiferin-6-O-berberine salt gels.

Example 10: Preparation of Mangiferin-6-O-Berberine Salt Freeze-Dried Powder 40 g mannitol was weighed in an appropriate reactor and 200 ml water for injection was added. 0.2 g (0.1% w/v) needle activated carbon was added, then heated to 80° C. and mixed for 30 minutes, and was subjected to a 0.22-um millipore filter for filtration. finally, a filtrate was yielded for reserve. 10 g mangiferin-6-O-berberine salt dihydrate was weighed, and 100 ml tert-butyl alcohol was added and then mixed to make the mangiferin-6-O-berberine salt to dissolve. The solution of mangiferin-6-O-berberine salt was mixed with the mannitol solution, and water for injection was supplementary added to 1000 ml and was subjected to a 0.22-um millipore filter for filtration and bottling. Each bottle contained 10 mg mangiferin-6-O-berberine salt. The bottles were then frozen and dried, and subjected to plug vacuum pressing and capping. Finally, the products were yielded after labeling and packaging.

The present invention is further described with reference to Examples hereinafter, but practice of the present invention is not limited to such Examples.

INDUSTRIAL PRACTICABILITY

The preparation method according to the present invention solves the problem of the cost pressure and environmental issues which are brought due to use of a lot of organic solvents, and thus the preparation method according to the present invention is suitable for industrialized production.

What is claimed is:

1. A mangiferin-6-O-berberine salt, wherein the mangiferin-6-O-berberine salt has a structure as defined in the following formula (I):

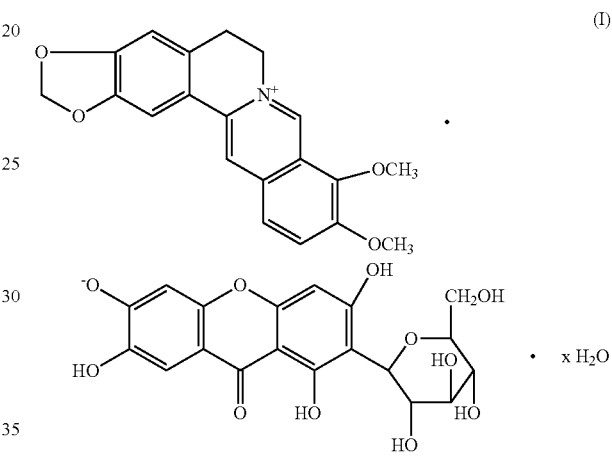

(I)

wherein 0≤x≤4;
wherein spectrum data of $^{13}$CNMR (400 MHz, DMSO-d6) δ of a mangiferin group of the mangiferin-6-O-berberine salt is as follows: 161.51 (C-1), 106.58 (C-2), 163.06 (C-3), 92.77 (C-4), 155.55 (C-4a), 103.74 (C-4b), 98.64 (C-5), 166.93 (C-6), 147.03 (C-7), 100.47 (C-8), 100.53 (C-8a), 154.37 (C-8b), 176.73 (C-9), 73.51 (C-1'), 70.34 (C-2'), 79.14 (C-3'), 70.34 (C-4'), 81.37 (C-5'), 61.27 (C-6').

2. The mangiferin-6-O-berberine salt according to claim 1, wherein x=2.

3. A preparation method for the mangiferin-6-O-berberine salt as defined in claim 1, comprising:
   (1) adding an alkaline sodium salt or a potassium salt into water to yield an alkaline aqueous solution of sodium salt or an alkaline aqueous solution of potassium salt, the solution having a concentration of 0.1%-2% (w/v);
   (2) dissolving mangiferin into dimethyl sulfoxide to yield a mangiferin solution;
   (3) slowly adding the mangiferin solution into the alkaline aqueous solution of sodium salt or the alkaline aqueous solution of potassium salt, fully stirring the solutions until the solutions are fully reacted at the temperature of 50° C.-100° C. to yield a mangiferin-6-O-sodium salt solution or mangiferin-6-O-potassium salt solution;
   (4) adding berberine hydrochloride into water at the temperature of 50° C.-100° C. to yield a solution of berberine hydrochloride;
   (5) fully mixing the solution of berberine hydrochloride with the mangiferin-6-O-sodium salt solution or mangiferin-6-O-potassium salt solution for full reaction, yielding a precipitate, filtering the precipitate to yield a solid; and (6) drying the solid to yield the mangiferin-6-O-berberine salt.

4. The preparation method according to claim 3, wherein a ratio of the mangiferin to the dimethyl sulfoxide is 1:0.2-5 (w/v).

5. The preparation method according to claim 3, wherein a molar ratio of the mangiferin to the alkaline sodium salt or alkaline potassium salt is 1:0.5-1.

6. The preparation method according to claim 3, wherein a molar ratio of the mangiferin-6-O-sodium salt or mangiferin-6-O-potassium salt to the berberine hydrochloride is 1:1.

7. The preparation method according to claim 3, wherein the alkaline sodium salt or alkaline potassium salt is one or a mixture of more than two selected from the group consisting of sodium carbonate, sodium bicarbonate, potassium carbonate and potassium bicarbonate.

8. A drug, wherein the drug comprises the mangiferin-6-O-berberine salt as defined in claim 1, and a pharmaceutically acceptable auxiliary material.

9. The mangiferin-6-O-berberine salt according to claim 1, wherein: the mangiferin-6-O-berberine salt is an AMPK activator.

10. The mangiferin-6-O-berberine salt according to claim 9, wherein the AMPK activator is used for a prevention or treatment of any one or more of the following diseases: diabetes, chronic diabetes complications, obesity, hyperlipidemia, insulin resistance, hyperinsulinemia, metabolic syndrome, hypertension, atherosclerosis, ischemic heart disease, myocardial hypertrophy, arrhythmia, heart failure, upper respiratory tract infection, chronic bronchitis, chronic obstructive pulmonary disease, asthma, pulmonary fibrosis, hepatitis, simple fatty liver, non-alcoholic fatty liver disease, non-alcoholic steatohepatitis, alcoholic liver, alcoholic hepatitis, liver fibrosis, cirrhosis, prostatitis, pancreatitis, nephritis, nephrotic syndrome, hypertensive nephropathy, chronic renal insufficiency, rheumatic arthritis, rheumatoid arthritis, osteoarthritis, inflammatory bowel disease, cerebral infarction, memory impairment, Alzheimer's disease, infarct dementia, Parkinson's disease, tumors, muscle atrophy, and muscle weakness disease.

11. The mangiferin-6-O-berberine salt according to claim 10, wherein the chronic diabetes complications comprise one or more diseases of: coronary heart disease, atherosclerosis, cerebrovascular disease; diabetic nephropathy, diabetic retinopathy; neuropathy; diabetic foot; diabetic maculopathy, cataracts, glaucoma, refractive changes, iris and ciliary body disease.

12. The drug according to claim 8, wherein the drug is used for a treatment of breast hyperplasia, uterine polyps, prostatic hyperplasia, sexual dysfunction, infertility, eczema, and fatigue.

13. The mangiferin-6-O-berberine salt according to claim 1, wherein x=1, 2, 3, or 4.

* * * * *